United States Patent [19]

Ferek-Petric

[11] Patent Number: 5,271,392
[45] Date of Patent: Dec. 21, 1993

[54] METHOD AND APPARATUS FOR ADMINISTERING CARDIAC ELECTROTHERAPY DEPENDENT ON MECHANICAL AND ELECTRICAL CARDIAC ACTIVITY

[75] Inventor: Bozidar Ferek-Petric, Zagreb, Croatia

[73] Assignee: Siemens-Elema AB, Sweden

[21] Appl. No.: 827,055

[22] Filed: Jan. 27, 1992

Related U.S. Application Data

[63] Continuation-in-part of Ser. No. 748,869, Aug. 23, 1991.

[30] Foreign Application Priority Data

Aug. 24, 1990 [YU] Yugoslavia .................. 1619/90

[51] Int. Cl.$^5$ .................................... A61N 1/362
[52] U.S. Cl. ....................................... 607/14
[58] Field of Search .............. 128/419 D, 419 PG

[56] References Cited

U.S. PATENT DOCUMENTS

| | | | |
|---|---|---|---|
| 3,815,611 | 6/1974 | Denniston, III | 128/419 D |
| 3,905,356 | 9/1975 | Fletcher et al. | 128/419 D |
| 3,942,534 | 3/1976 | Allen et al. | 128/419 PG |
| 4,114,628 | 9/1978 | Rizk | 128/419 D |
| 4,291,707 | 9/1981 | Heilman et al. | 128/784 |
| 4,475,551 | 10/1984 | Langer et al. | 128/419 D |
| 4,535,774 | 8/1985 | Olson | 128/419 G |
| 4,572,191 | 2/1986 | Mirowski et al. | 128/419 D |
| 4,600,017 | 7/1986 | Schroeppel | 128/419 D |
| 4,614,192 | 9/1986 | Imran et al. | 128/419 D |
| 4,662,377 | 5/1987 | Heilman et al. | 128/419 D |
| 4,686,987 | 8/1987 | Salo et al. | 128/419 PG |
| 4,690,143 | 9/1987 | Schroeppel | 128/602 S |
| 4,763,646 | 8/1988 | Lekholm | 128/419 PG |
| 4,766,902 | 8/1988 | Schroeppel | 128/419 PG |
| 4,768,511 | 9/1988 | DeCote, Jr. | 128/419 PG |
| 4,768,512 | 9/1988 | Imran | 128/419 D |
| 4,770,177 | 9/1988 | Schroeppel | 128/419 PG |
| 4,773,401 | 9/1988 | Citak et al. | 128/419 PG |
| 4,774,950 | 10/1988 | Cohen | 128/419 D |
| 4,779,617 | 10/1988 | Whigham | 128/419 D |
| 4,784,151 | 11/1988 | Frank et al. | 128/675 |
| 4,790,317 | 12/1988 | Davies | 128/419 PG |
| 4,791,931 | 12/1988 | Slate | 128/419 PG |
| 4,798,206 | 1/1989 | Maddison et al. | 128/419 D |
| 4,856,523 | 8/1989 | Sholder et al. | 128/419 PG |
| 4,895,151 | 1/1990 | Grevis et al. | 128/419 D |
| 5,097,830 | 3/1992 | Eikefjord et al. | 128/419 D |
| 5,109,842 | 5/1992 | Adinolfi | 128/419 D |

FOREIGN PATENT DOCUMENTS

WO88/09684 12/1988 PCT Int'l Appl. .

OTHER PUBLICATIONS

"Transducer for Cardiovascular Research," Feldstein et al., Mechanical Engineering, Apr. 1976, p. 57.
"Transducers for Heart Research," Feldstein et al., NTIS Tech Notes, May 1985, p. 519.

Primary Examiner—William E. Kamm
Attorney, Agent, or Firm—Hill, Steadman & Simpson

[57] ABSTRACT

A method for administering cardiac electrotherapy and an implantable electrotherapy apparatus employ myocardial tensiometry to measure contractions of the heart muscle. The system includes a tensiometric element disposed at a location subject to bending due to cardiac contractions, the tensiometric element consisting either of piezoelectric material or variable resistivity material, the mechanical stresses to which the tensiometric element is subjected causing the element to produce a voltage or a resistivity variation comparable in frequency and amplitude to the contractions. The tensiometric element may be in the form of a strip disposed on a surface of a patch electrode, of the type suitable for use in an implantable defibrillator, or may be a strip or a tube located at the bend of a J-shaped pacing lead, of the type implantable in the atrium or in the ventricle in a cardiac pacemaker system. Electrical cardiac activity due to repolarization of the cardiac tissue is also sensed, and the frequency of the electrical activity, the frequency of the mechanical activity due to the cardiac contractions, and the amplitude of the voltage signal produced by the tensiometric element are used to control the administration of electrotherapy to the cardiac tissue.

8 Claims, 9 Drawing Sheets

METHOD AND APPARATUS FOR ADMINISTERING CARDIAC ELECTROTHERAPY DEPENDENT ON MECHANICAL AND ELECTRICAL CARDIAC ACTIVITY

This is a continuation-in-part of application Ser. No. 748,869, filed Aug. 23, 1991.

BACKGROUND OF THE INVENTION

FIELD OF THE INVENTION

This invention relates to cardiac pacemakers and implantable cardioverters-defibrillators, more particularly to improved detection of pathologic tachycardias and fibrillation, as well as to more physiologic sensor for rate responsive pacing and accurate detection of pacing capture.

BACKGROUND AND PRIOR ART

Tachycardia is a condition in which the heart beats rapidly. Pathologic tachycardia is hemodynamically disturbing, causing the drop of systemic blood pressure. There are many types of pathologic tachycardias and the electrophysiology differentiates two major classes: supraventricular and ventricular tachycardias. Tachycardia is often the result of electrical feedback within the heart structures where the natural beat results in the feedback of an electrical stimulus which prematurely triggers another beat. There are several different cardiac pacing modes which may terminate tachycardia. The underlying principle in all of them is that if a pacemaker stimulates the heart at least once shortly after a heartbeat, before the next naturally occurring heartbeat at the rapid rate, the interposed stimulated heartbeat disrupts the stability of the feedback loop thus reverting the tachycardia to sinus rhythm. Such a pacemaker is disclosed in U.S. Pat. No. 3,942,534 which, following detection of tachycardia, generates a stimulus after a delay interval.

The most hazardous arrhythmia is ventricular tachycardia which may progress into life-threatening arrhythmia ventricular fibrillation. Because ventricular tachycardia is not always successfully treated and terminated by antitachycardia pacing, the implantable cardioverter-defibrillator is used to deliver a high energy pulse shock to cause cardioversion of ventricular tachycardia to sinus rhythm. Such an implantable device is disclosed in U.S. Pat. No. 4,614,192 having a bipolar electrode for R-wave sensing, the system utilizing heart rate averaging and a probability density function for fibrillation detection. A similar system for cardioversion is disclosed in U.S. Pat. No. 4,768,512 which has high frequency pulse delivery. All these systems deliver high energy shock through the special patch-electrodes such as described in U.S. Pat. No. 4,291,707. To simplify the surgical procedure, systems having a superior vena cava electrode and subcutaneous electrode, such as described in U.S. Pat. No. 4,662,377, have been developed. The supraventricular tachycardia caused by atrial flutter or fibrillation can be also treated by an implantable cardioverter such as described in U.S. Pat. No. 4,572,191.

The difficulty in electrotherapy treatment of tachycardia is that the implantable apparatus has to include means for accurately detecting pathologic tachycardia so as to deliver the electrotherapy pulses whenever the pathologic tachycardia occurs. A problem is that the heart rhythm increases its repetition rate physiologically whenever either physical or emotional stress occurs. The means for pathologic tachycardia detection must accurately differentiate the natural sinus tachycardia, which should not be treated by means of electrotherapy from the pathologic tachycardia which has to be treated. Therefore discrimination between normal and pathologic tachycardia on the basis of rate measurement is not reliable. To overcome this problem numerous methods of tachycardia detection have been developed which are applicable in implantable electrotherapy devices.

Such a system is disclosed in U.S. Pat. No. 4,475,551 wherein heart rate sensing as well as a probability density function are used to distinguish between ventricular fibrillation and high rate tachycardia. Another system is disclosed in U.S. Pat. No. 4,790,317 which can automatically recognize the pathologic rhythm by monitoring the pulse sequence representing the ventricular electrical activity. At least two sensing positions i.e. for each ventricular epicardial surface, are used, but more sensing points will obtain better discrimination between normal and pathologic rhythms.

The problems which may occur with such systems are susceptibility to electromagnetic interference and muscular noise, as well as improper gain of the heart beat detectors causing the undersensing of cardiac rhythm. Therefore some means for detecting of noise and means for automatic sensitivity adjustment are desirable. Therefore the implanted pacemaker noise rejection system described in U.S. Pat. No. 4,779,617, as well as the automatic sensitivity control systems disclosed in U.S. Pat. No. 4,766,902 and U.S. Pat. No. 4,768,511 have been developed.

The implantable cardioverting system usually includes a cardiac pacing system because of the occurrence of bradycardial events which follow the cardioversion high voltage pulse. There are also patients who suffer from pathologic tachycardia as well as from bradycardia, to be treated by cardiac pacing. Therefore a physiological sensor for control of the heart rate is desirable to obtain rate responsive pacing. It is also possible for the cardioversion device to have a dual chamber physiologic pacing function. In such a system, a sensor for atrial fibrillation detection would be important not only for the appropriate ventricular response to atrial rhythms, but also for differentiating supraventricular from ventricular tachycardia. There are many physiological control systems for rate responsive pacing, but only few of them can be used for tachycardia detection as well. As far as is known, none of these sensor systems can be used for ventricular tachycardia detection, rate responsive pacing, atrial fibrillation detection, pacing capture and for noise detection. The system disclosed in U.S. Pat. No. 4,774,950 has a circulatory systemic blood pressure measurement system which detects a drop of pressure in the case of pathologic heart rhythm. A similar system is described in U.S. Pat. No. 4,791,931 wherein the pressure is measured by means of arterial wall stretch detection. Another system disclosed in U.S. Pat. No. 4,770,177 adjusts the pacing rate relative to changes in venous blood vessel diameter that is measured by a piezoelectric sensor. The heart contractions change the ventricular chamber volume due to the inflow and outflow of blood thus varying the impedance within the chamber. Impedance measurement is used in the system described in U.S. Pat. No. 4,773,401 to obtain physiological control of pacing rate. Furthermore stroke volume and ventricular volume measurement are possible in the system described in U.S. Pat. No. 4,686,987 as well as in U.S. Pat. No. 4,535,774. All these systems indirectly measure the mechanical contraction of the heart which is a consequence of the electrical depolarization and which is influenced by the sympathetic and parasympathetic nervous system as well as by circulatory cathecholamines. The sympathetic stimulation and circulatory cathecholamines increase the speed of the contraction and therefore the hemodynamic forces are accordingly transferred to the circulatory system. In the case of pathologic rhythm having an electric depolarization disturbance, hemodynamics will be impeded.

The quality of the mechanical cardiac contraction significantly differs in normal and pathologic rhythms. Therefore a system for direct measurement of parameters of mechanical cardiac contraction would be desirable because it would obtain more exact physiological parameters, which may be used for a rate responsive pacing algorithm as well as for detection of different cardiac rhythms. The system disclosed in U.S. Pat. No. 4,784,151 has a conductive rubber tube whose changes in resistance are measured, which are caused by tube distension. In such a system the cardiac contraction energy is transformed into the hemodynamic energy and again into the mechanical distension movements.

The system disclosed in U.S. Pat. No. 4,763,646 discloses a pacing lead having a sensor for heart sound, pressure and acceleration. The sound and pressure are physically of the same origin and only the frequency spectra are different. Therefore it is easy to detect both parameters with the same transducer by filtering of its signal, where the signal at the output of the low-pass filter is pressure, while the signal at the output of the high-pass filter is sound.

SUMMARY OF THE INVENTION

According to the present invention a system for myocardial tensiometry is incorporated within the implantable electrotherapy apparatus in order to achieve measurement of the mechanical contractions of the heart muscle. The tensiometric system is formed by an elastic strip made of either piezoelectric material or resistive material, wherein the mechanical stress to which the strip is subjected produces either an electric voltage or a variable resistivity, respectively.

It is, therefore, an object of this invention to provide a device having the aforementioned elastic tensiometric strip mechanically coupled to the heart muscle.

It is, also, an object of this invention to provide a device with the capability of either analyzing the electric signal or measuring the resistivity variations produced within the tensiometric strip and caused by means of the cardiac muscle contractions.

It is an object of this invention to provide a device with the capability to monitor the mechanical activity of the heart in order to check whether the pacing pulse is followed by a mechanical contraction.

A further object of this invention is to provide a device for detection of the mechanical movements of a heart which are characteristic for a certain type of cardiac rhythm, thus enabling exact detection of the pathologic cardiac rhythm.

It is another object of this invention to provide a sensor indicating physical stress for The measurement of acceleration is physically the most alike to the system disclosed in herein. However, there is a significant difference between measurement of the lead acceleration and the lead tension. The output signal of an accelerometer is a function of the first derivative of the lead movement velocity, the vector of this velocity being perpendicular to the lead axis. This is because of the fact that the implanted lead, especially after the fixation within the heart by means of the fibrotic tissue, can move relative to the heart radially to the lead assembly. The signal from an accelerometer is influenced by two components: the radial intracardiac acceleration of the lead caused by the cardiac contraction and the multi-directive acceleration of the entire human body caused by either the body movements of the body transport. Therefore the practical application of an accelerometer has the problems of oversensing of the human body acceleration which very much impedes accuracy, specificity and sensitivity of the sensor. The sensitivity relation in favor of external acceleration rises especially in the chronic phase of cardiac pacing, when the lead is enclosed within the fibrotic channel which significantly attenuates the radial acceleration component caused by the cardiac contraction. Furthermore, the radial acceleration of the lead at the point of accelerometer fixation is influenced by the intracardiac blood stream in such a way as to attenuate direct energy transfer from cardiac muscle to the accelerometer. Assuming that the lead is implanted in the middle of the intracardiac cavity in such a way as to enable radial movements within the right ventricle, the cardiac contraction energy is transferred to the lead primarily at the lead tip. Therefore, the elastic lead body also attenuates the energy transfer between the accelerometer and the lead tip.

Contrary to the known systems, in the system disclosed herein, the cardiac contraction energy is transformed directly into the mechanical stretching energy within the transducer thereby producing the measurement and processing signal within the transducer, which is mechanically coupled to the heart muscle. Therefore, cardiac contraction provides the signal having amplitude and frequency characteristics representing the same characteristics as the contraction itself, consequently enabling signal processing in such a way as to obtain information about the contraction amplitude and velocity as parameters for cardiac electrotherapy control. There is no external mechanical energy which can impede the tensiometry signal, and there is no significant influence of the fibrotic tissue on the signal.

The system disclosed in U.S. Pat. No. 4,600,017 discloses lead having a piezoelectric sensor for monitoring the cardiac contractions. Disclosed system can sense either the pressure or the sound which are the consequence of the cardiac muscle contraction. It is possible to generate a signal which may be used for measurement of cardiac cycle timing parameters such as the period of isometric contractions, ejection time etc. It is not possible to measure the cardiac muscle contraction forces directly as is possible in the system disclosed herein.

The system disclosed in U.S. Pat. No. 4,690,143 discloses a lead having a piezoelectric strip for generating electrical power for cardiac electrotherapy. Because a larger quantity of piezoelectric material produces a greater amount of electrical power, the strip is mounted within the lead through the entire distal end of the lead in the heart form superior vena cava to the right ventricular apex, or as a spiral strip to increase the strip length. The strip has to be isolated from any internal lead conductors. In the system disclosed in the present application, a specific position and length of the piezoelectric strip are required only in the lead bending area, so as to specifically measure only the ventricular contraction forces. In the system herein the pacing-sensing lead wire is used for the piezoelectric strip connection and therefore the lead has only one more lead wire above the conventional number of electrodes in the specific lead i.e. two lead wires in a unipolar lead.

Furthermore, in the system disclosed herein, there is the possibility to use a standard pacing lead for tensiometric measurement. Normally, the stylet channel of a lead enables the control of the lead implantation by means of a steel wire (stylet) insertion. Manipulating the stylet i.e. rotating, pushing and pulling governs the direction of the lead tip. After the proper positioning of the lead tip, the stylet is pulled out. Therefore every implanted lead has an empty stylet channel which may be used for the permanent insertion of a tensiometric stylet.

Moreover, the system disclosed herein may use not only the piezoelectric voltage generation but also the variable resistance as a tensiometric parameter the purpose of rate responsive cardiac pacing.

DESCRIPTION OF THE PREFERRED EMBODIMENT

Figure 1:
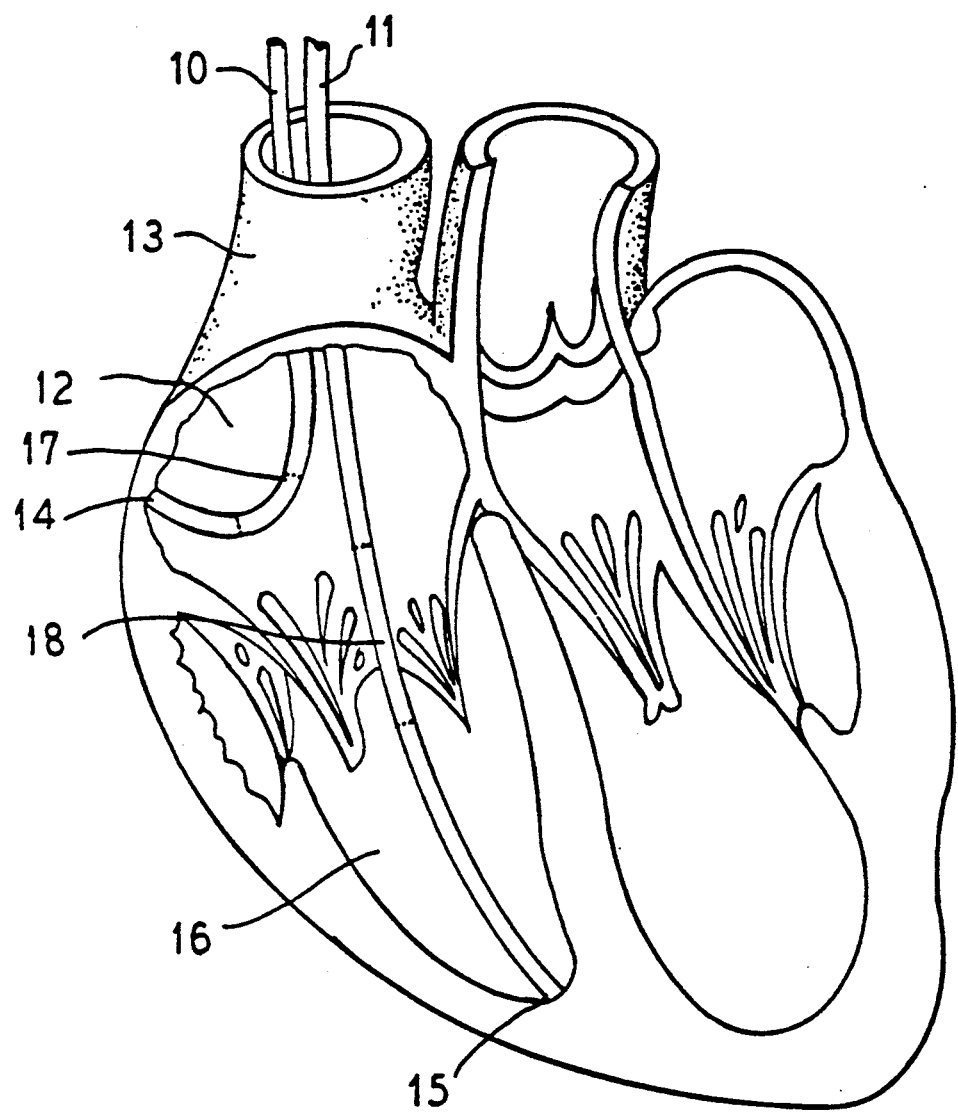
FIG. 1 is a cross-sectional four-chamber view of a human heart having an atrial as well as a ventricular pacing lead implanted therein constructed in accordance with the principles of the present invention.

In the embodiment of FIG. 1 there is shown a four-chamber cross-section of the human heart having an atrial pacing lead 10 and a ventricular pacing lead 11 implanted therein. Both leads enter the right atrium 12 through the superior vena cava 13. The atrial lead 10 is a J-shaped lead having an electrode 14 at its tip which is positioned in the right atrial appendage. The ventricular lead 11 has an electrode 15 at its tip which is positioned in the right ventricle 16 in the apical position. Though unipolar leads are disclosed, bipolar leads can alternatively be implanted in the same anatomic relation to the heart chambers. Every contraction of the heart muscle deflects both pacing leads. The atrial contraction causes bending of the atrial lead 10 while the ventricular contraction causes bending of the ventricular lead 11. The magnitude of the lead deflection depends on the radial lead stiffness and on the heart muscle contraction forces. It also depends on the initial bending forces caused by the specific implantation position. For instance, the atrial lead 10 implanted in the appendage will have a smaller J-shape radius than a lead implanted on the anterior atrial wall. If the lead body is pre-shaped to the J-shape, the lead body will bear lower tension forces if implanted in the atrial appendage than if implanted on the atrial wall or septum. By contrast, if the lead body is straight, a lead in the appendage will bear greater body tension than a lead implanted on the anterior wall or interatrial septum. Depending on the transatrial loop radius, the ventricular lead 11 will bear some initial bending tension forces. Because of the cardiac muscle contractions, the lead body has to bear additional dynamic tension forces. Every implanted lead has a section which is the part the lead primarily exposed to the bending caused by the cardiac contractions. This bending section is clearly visible on X-ray diascopy of leads, especially if a surgeon adjusts the optimal loop of the ventricular lead, thus changing the magnitude of the bending deflection. The bending section 17 of the lead 10 implanted in the right atrial appendage is shaded gray, as is the bending section 18 of the ventricular lead 11. Especially in the chronic phase of cardiac pacing when fibrotic tissue anchors the lead tip to the endocardium, the lead is strongly mechanically coupled to the heart muscle. Therefore the myocardial movement forces are transferred to the lead with inconsequential losses caused by the lead elasticity which attenuates these forces. It is known that various cardiac rhythms have different hemodynamics, which means different magnitudes of contraction movements as well as different frequency spectra of these movements. For example, ventricular tachycardia impedes the cardiac contractions significantly, causing a decrease in the contraction magnitude. Different cardiac rhythms cause various forces which result in the implanted lead experiencing mechanical tension. The aim of the present invention is to enable the measurement of the implanted lead tension and thereby detect and differentiate various cardiac rhythms. Two different methods may be used for this purpose depending on the sensor for the tension measurement. The first method is to use elastic conductive material which changes the resistivity as a means of elastic distension. The second method is to use a piezoelectric transducer which produces voltage as a result of the elastic bending.

Figure 2:
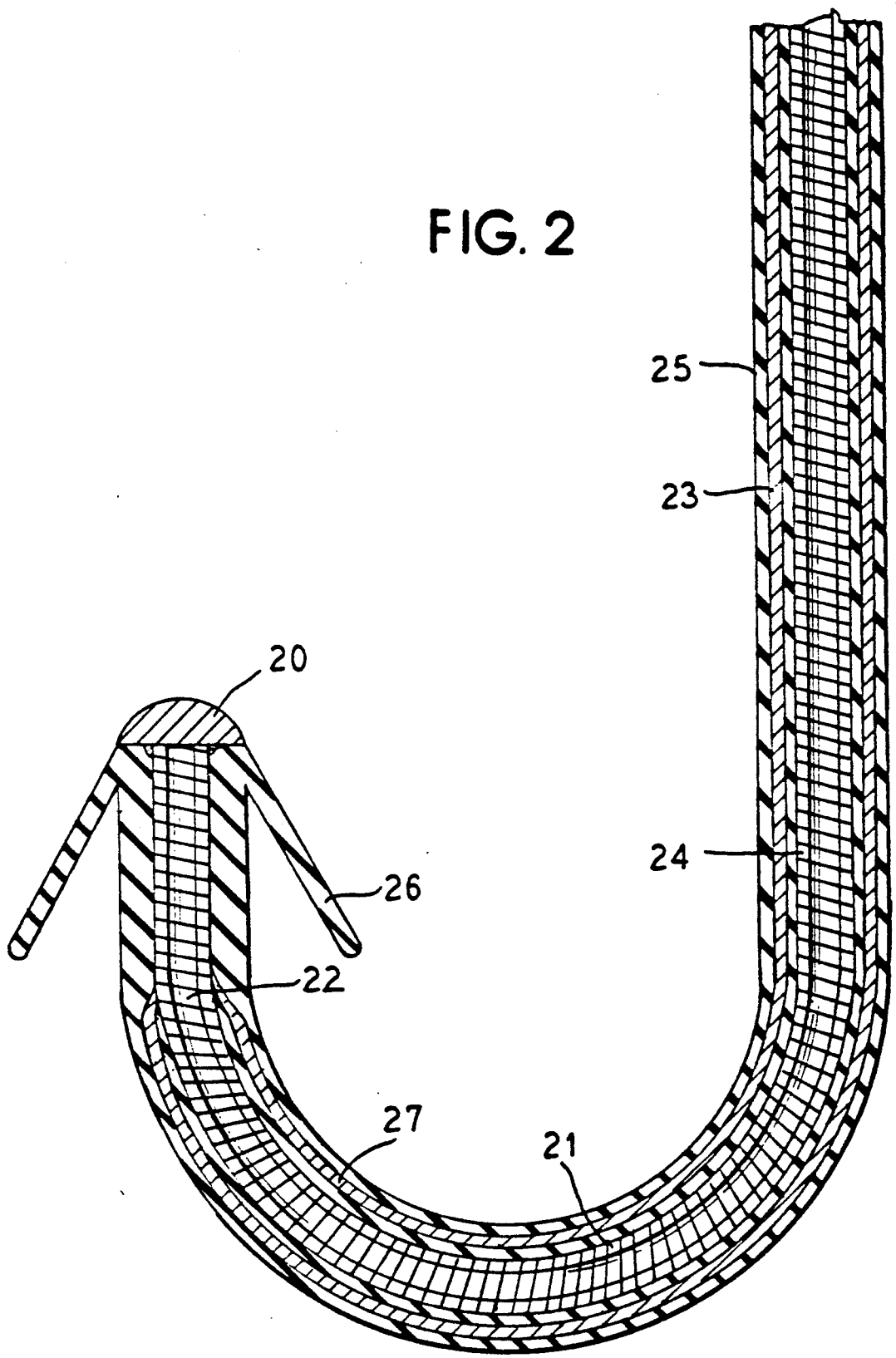
FIG. 2 is a cross-sectional view of a unipolar atrial J-shaped pacing lead with a tensiometric strip in the bending sector constructed in accordance with the principles of the present invention.

In the embodiment of FIG. 2, there is shown a distal part of a J-shaped unipolar pacing lead having an electrode 20 at the tip. The electrode 20 is electrically connected with the central pin of a connector (not shown) at the proximal part of the lead (not shown) by means of the lead conductor 21 having a stylet channel 22. The lead has another coaxial lead conductor 23 which is connected with the ring of the same connector (not shown). Two helically wounded lead conductors are isolated by means of an inner insulation 24 and an outer insulation 25. The surface of the outer insulation 25 may have some means for lead fixation at the tip of the lead. In the disclosed embodiment, tines 26 are shown only for example. Within the area of mechanical stress of the lead caused by the bending, there is a tensiometric tube 27. The tensiometric tube 27 is in the disclosed example assembled to the lead in such a way as to proceed through the lumen of the outer lead conductor 23 being electrically connected to the outer conductor 23 at the point of distal end of the conductor 23 and proximal end of the tube 27. The distal end of the tensiometric tube 27 is electrically connected to the inner lead conductor 21. The tensiometric tube is also isolated by the insulations 24 and 25. The tensiometric tube 27 is electrically connected to the control electronic circuits of an electrotherapy device (not shown) by means of both lead conductors 21 and 23. In the exemplary unipolar configuration the electrode 20 is electrically connected to the electrotherapy circuits of an electrotherapy device by means of the inner lead conductor 21. The bipolar lead should have three lead conductors in order to achieve the proper connection, wherein one conductor should be used only for connection of the tensiometric sensor while one other conductor is common for tensiometric sensor as well as for an electrode, and the third conductor is only used for another electrode.

Figure 3:
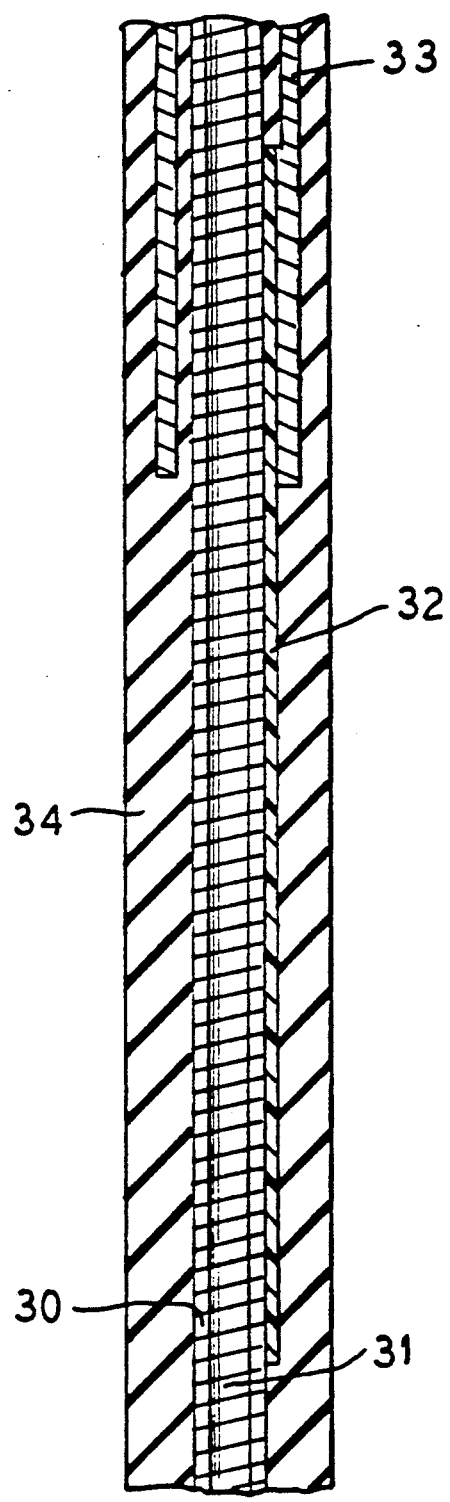
FIG. 3 is a cross-sectional view of an unipolar ventricular lead with a tensiometric strip in the bending sector, constructed in accordance with the principles of the present invention.

In the embodiment of FIG. 3 there is shown a cross-section of a tensiometric section of an unipolar ventricular lead. The distal end having the active electrode and the proximal end having the connector assembly are not shown. The lead has a lead conductor 30 with a stylet channel 31. The lead conductor 30 connects the active electrode with the corresponding pin on the connector assembly. A section of a tensiometric strip 32, for example made of Kynar ® Piezo Film (Pennwalt Corporation, Valley Forge, Pa.), is mounted tight to the lead conductor 30. Materials such as Kynar ® film have conductive surfaces in order to obtain an electrical connection either by means of either soldering or conductive gluing of electrical conductors on both surfaces. Therefore the lead conductor 30 is tight with the tensiometric strip 32, or conductively glued in such a way as to obtain the electric connection between one surface of the film strip 32 and lead conductor 30. In the disclosed embodiment the lead has helically wounded coaxial lead conductors.

Another surface of the film strip 32 is tight with the outer lead conductor 33 so as to obtain an electric connection between the another conductive surface of the tensiometric film strip 32 and the outer lead conductor 33. In disclosed lead assembly, the electrical connection of the film strip 32 with the connector assembly (not shown) and thus to the control electronic circuits of an electrotherapy device (not shown), is obtained by means of the lead conductors 30 and 33, while the electrical connection of an electrode at the lead tip (not shown) with a corresponding pin on the connector assembly (not shown), and thus to the electrotherapy circuits of an electrotherapy device (not shown), is obtained by means of inner lead conductor 30. The lead body 34 is made of insulation material (either polyurethane or silicone), as it is known in the art, in such a way as to obtain the electrical insulation between the two lead conductors as well as between the lead conductors and the human body tissues and fluid. The disclosed example illustrates the principle of a unipolar tensiometric lead such as the ventricular lead 11 from FIG. 1, but the same principle can be applied to the design of a bipolar pacing lead or a multipolar helical-coil lead for an implantable defibrillator. Always, the electrical connection of the tensiometric transducer is obtained in such a way as to use one extra lead conductor for one pole of the transducer and one other lead conductor, which is connected to the one of lead electrodes, for another pole of the transducer. This kind of connection assembly, using one common lead conductor for one pole of the transducer and for one electrode, requires only one additional lead conductor beyond the number of lead conductors normally used in the specific lead type. In all of the examples from previous figures, different kinds of transducers may be used. Tensiometric tube as well as a tensiometric strip can be made of conductive rubber or any other material which changes its conductivity because of distension. In such a design the electrotherapy device has to include electronic circuits for measurement of the transducer resistance and analysis of the resistance changes in such a way as to enable detection of various cardiac arrhythmias. Tensiometric tubes and strips can be also made of piezoelectric material which produces an electric voltage because of distension. In this kind of design the electrotherapy device has to include electronic circuits for measurement and analysis of the transducer signal, thereby enabling the detection and differentiation of various cardiac arrhythmias.

Figure 4:
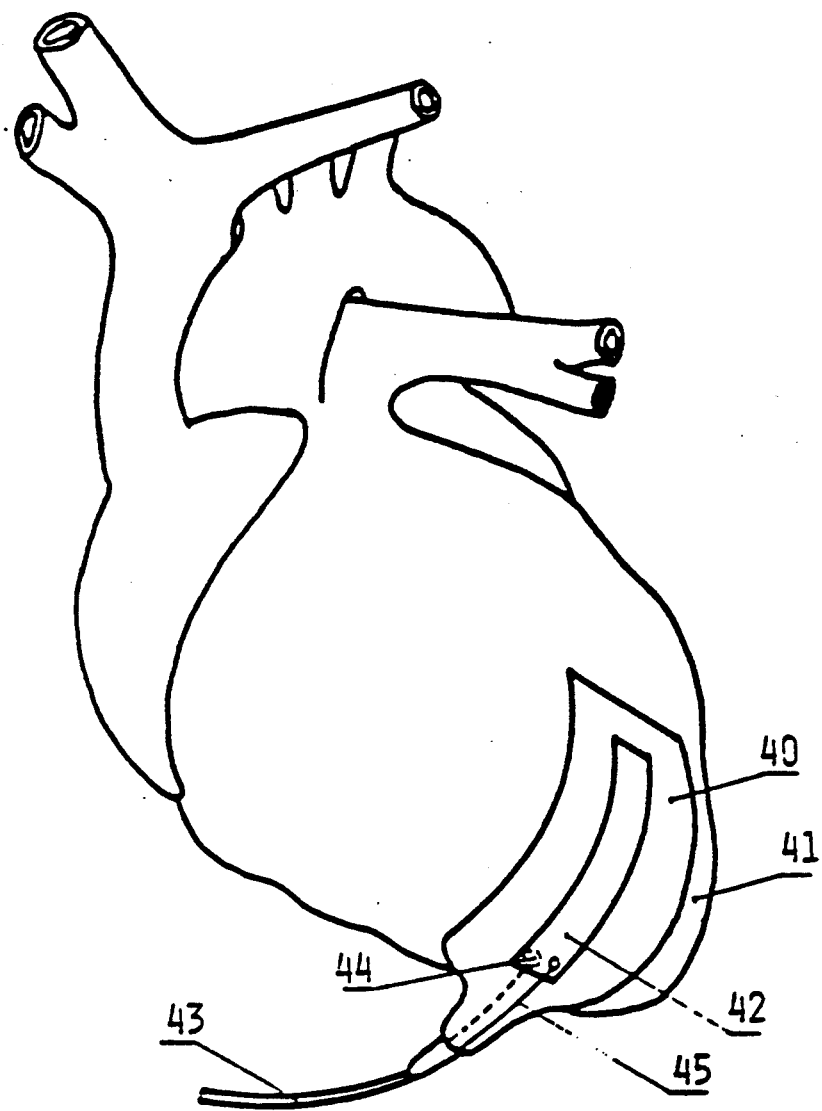
FIG. 4 is a perspective view of a human heart having an implanted defibrillator patch with a tensiometric strip, constructed in accordance with the principles of the present invention.

In the embodiment of FIG. 4, there is shown a perspective view of a human heart having a defibrillator patch 40 implanted on the apex 41. The patch 40 has a tensiometric strip 42 mounted fixed within the patch body. The tensiometric strip transducer 42 can be made of elastic material which either changes resistivity or produces voltage upon the mechanical distension. In disclosed patch assembly, the tensiometric strip 42 is bent in the rhythm and local pattern of cardiac contractions. In the case of ventricular tachycardia or fibrillation, the local pattern of contractions will be changed, consequently producing different transducers signal in comparison with the sinus rhythm. The electrical connection in the exemplary embodiment of FIG. 4 is suitable, for example, when the piezoelectric film strip is used such as Kynar ® Piezo Film. The patch lead 43 has two electrical lead conductors. The first lead conductor 44, (designated by dashed lines) is electrically connected to the conductive mesh (not shown) which has direct contact with epicardium, and to the surface of tensiometric strip 42 which is mounted on the conductive mesh. The second lead conductor 45 is electrically connected to the opposite surface of the tensiometric strip 42. In the disclosed electric connection assembly, the lead conductor 44 connects the defibrillating electrode (conductive mesh) and one pole of tensiometric transducer 42 to the electronic circuits (not shown), and the lead conductor 45 connects the another pole of the tensiometric transducer 42 to the electronic circuits of an implantable defibrillator (not shown).

Figure 5:
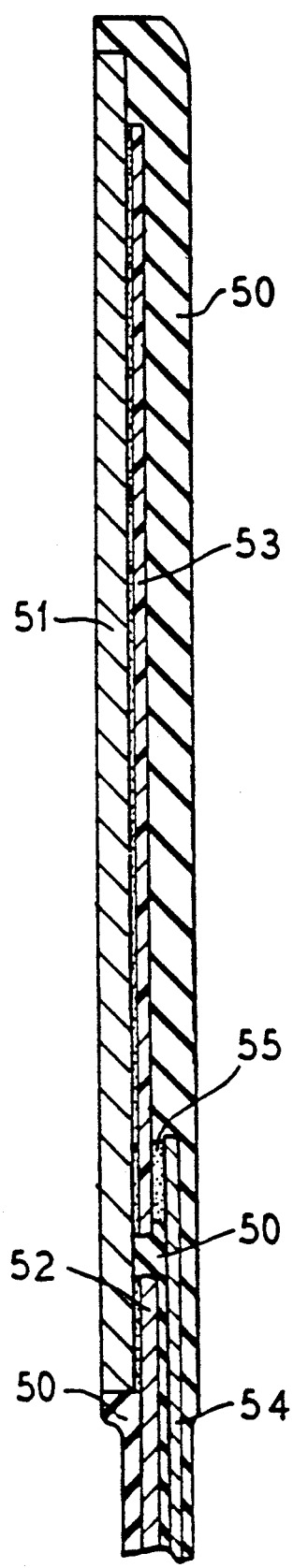
FIG. 5 is a cross-sectional view of a defibrillator patch having a tensiometric strip, constructed in accordance with the principles of the present invention.

In the embodiment of FIG. 5, there is shown a cross-section of defibrillator patch from FIG. 4. The patch is formed of elastic insulation material 50, usually silicon rubber. The conductive surface 51 is the defibrillating electrode, usually made of wire mesh. A lead conductor 52 is electrically coupled to the electrode 51 and electrically connects the electrode 51 to the electrotherapy circuit of an implantable defibrillator (not shown). One surface of the tensiometric strip 53 is mounted tight to the electrode 51 in such a way as to assure the electrical connection between the one pole of the transducer 53 and the electrode 51. Conductive gluing or even soldering may be used for this purpose. A second lead conductor 54 is electrically connected to the another pole of the transducer 53 by means of either conductive gluing or soldering junction 55. In the embodiment of FIG. 5, both lead conductors connect the transducer 53 to the control electronic circuits of an implantable defibrillator (not shown). The systems in accordance with the invention disclosed thus far are intended for use only in primary implantations. The following examples have the significant advantage of enabling the system to convert the standard chronically implanted lead into a tensiometric lead. Such a system has a specially designed tensiometric stylet which is inserted into the existing lead channel in such a way as to enable the electric connection of the tensiometric stylet by means of an existing central pin of a lead connector and an additional stylet connector pin.

Figure 6:
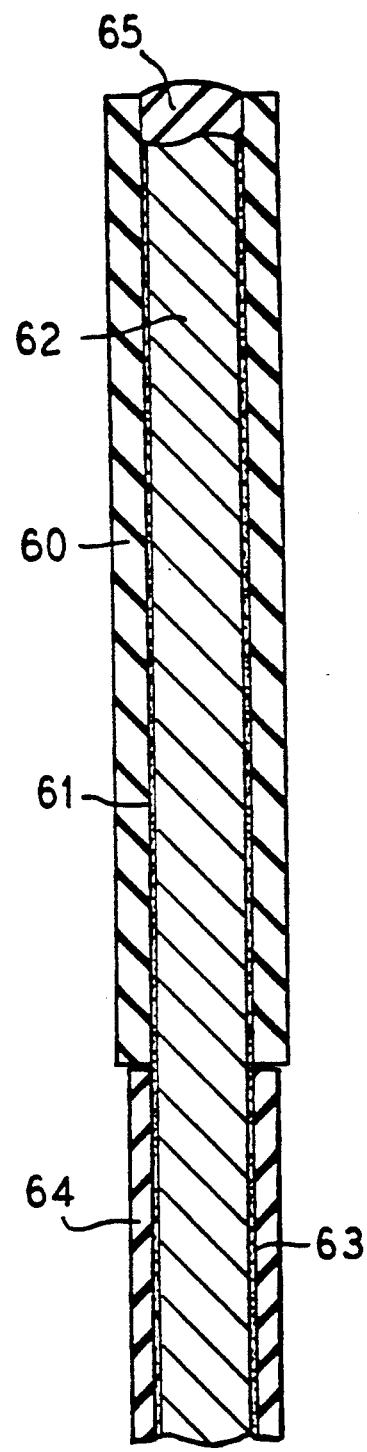
FIG. 6 is a cross-sectional view of the distal end of a tensiometric lead stylet with a tensiometric tube, constructed in accordance with the principles of the present invention.

In the embodiment of FIG. 6 there shown, in cross-section, the distal end of a tensiometric stylet having a tensiometric tube 60. The tube 60 is made of an elastic material, such as conductive rubber or some piezoelectric material. The external surface of the tube 60 has a diameter which makes electrical contact with the lead conductor which forms the stylet channel (not shown). The internal surface of the tube 60 is glued by means of a conductive adhesive layer 61 to the stylet wire 62 which is insulated by an insulation 63. The joint between the insulation 63 and the tube 60 is glued by means of an insulative adhesive layer 64. The stylet tip is closed by a silicone stopper 65. When the stylet is inserted within the lead (not shown) through its stylet channel, the outer surface of the tube 60 slides through the channel having mechanical as well as electrical contact with the inner surface of the lead conductor. If the tube 60 is made of the conductive rubber, the radial impedance of the tube can be measured between the central lead conductor and the stylet conductor 62. If the tube 60 is made of piezoelectric material, a voltage will be generated between the same conductors. The length of the stylet is selected so as to position the tube 60 within the lead bending area.

Figure 7:
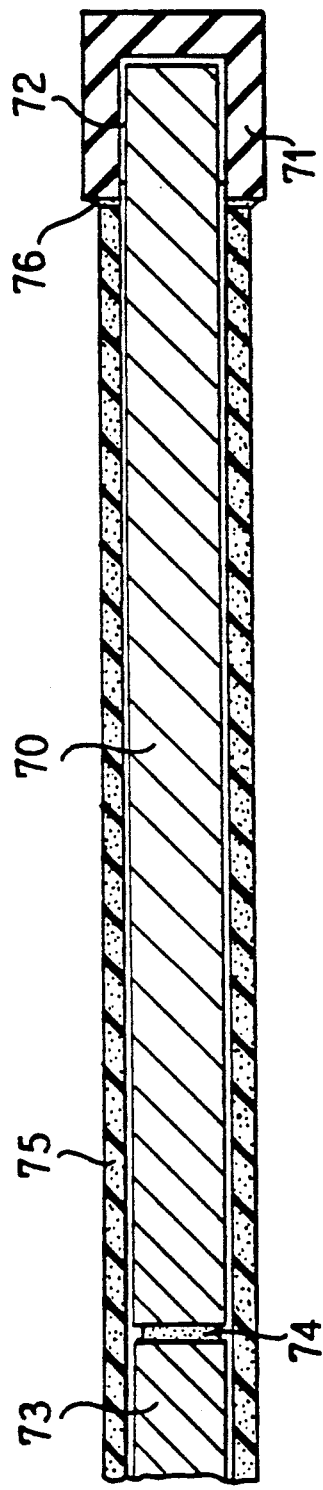
FIG. 7 is a cross-sectional view of the distal end of a tensiometric lead stylet having a tensiometric cylinder, constructed in accordance with the principles of the present invention.

In the embodiment of FIG. 7 there is shown a cross-section view of the distal end of a tensiometric stylet having a tensiometric cylinder 70. The cylinder 70 is made either of conductive rubber or of elastic piezoelectric material. There is a conductive, preferably metallic, hollow stopper 71 at the distal end of the stylet. The cylinder 70 is partially embedded within the stopper 71. The stopper 71 is electrically connected with the distal end of the cylinder 70 by means of a conductive adhesive layer 72. The proximal end of the cylinder 70 is electrically connected to a wire 73 by means of either a conductive adhesive layer or a soldering joint 74. An insulation 75 of the electric wire 73 is elongated in such a way as to obtain the insulation of the cylinder 70. At its distal end, the insulation 75 is glued to the stopper 71 by means of an adhesive layer 76. The outer diameter of the stopper 71 is trimmed in such a way as to ensure the electrical contact with the pacing lead conductor (not shown) when the disclosed stylet is slides within the stylet channel of the said lead. Therefore the longitudinal resistance of the cylinder 70 can be measured between the stylet wire 73 and the central lead conductor.

Figure 8:
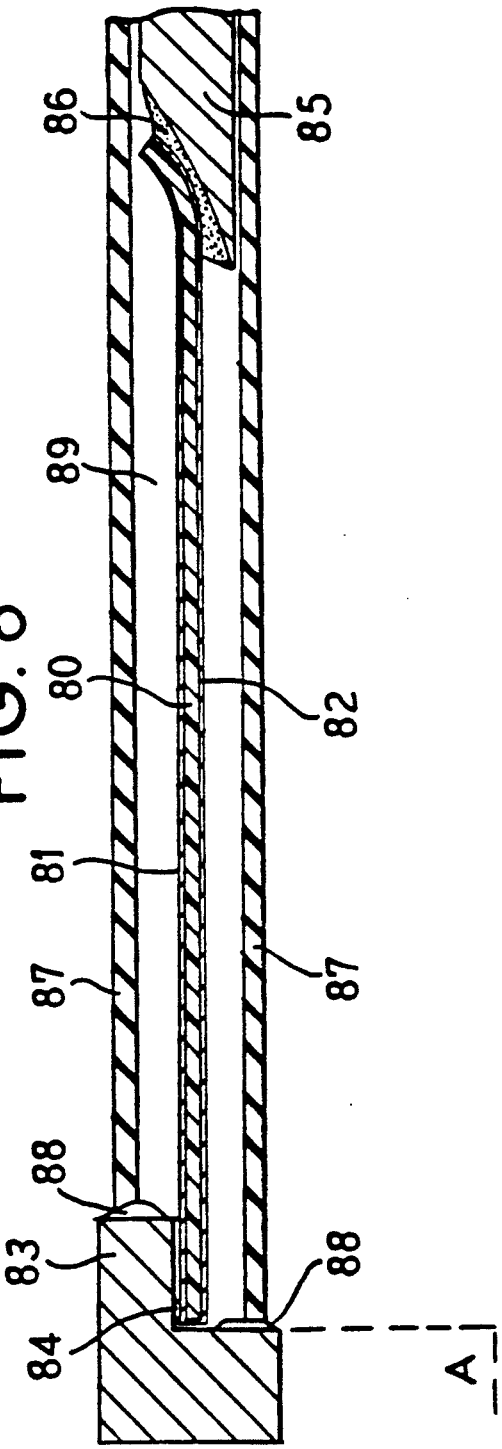
FIG. 8 is a cross-sectional view of the distal end of a tensiometric lead stylet having a tensiometric strip, constructed in accordance with the principles of the present invention.
Figure 9:
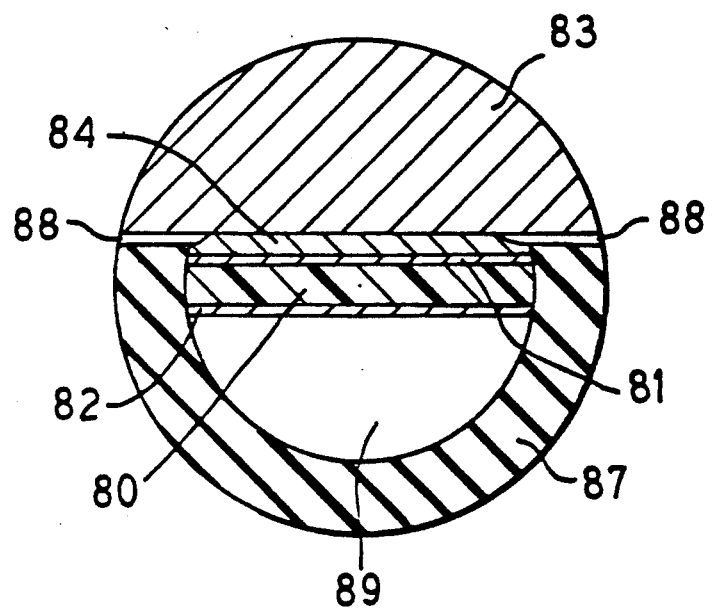
FIG. 9 is a cross-sectional view of the distal end of the lead stylet of FIG. 8.

In the embodiment of FIG. 8 a cross-section of the distal end of a tensiometric stylet is shown having a tensiometric strip 80. The strip 80 is a piezoelectric material, such as the Kynar® piezo film, having two metallized layers 81 and 82 on its opposing surfaces forming the electrodes of the piezo film. The distal end of the stylet is formed by a metallic cylinder 83 having a portion cut out. The outer diameter of the cylinder 83 is trimmed to ensure electrical contact with the pacing lead conductor (not shown) when the disclosed stylet slides within the stylet channel of the lead. A strip electrode 81 is electrically connected to the cylinder 83 by means of a soldering joint 84. The strip electrode 82 is electrically connected to a stylet wire 85 by a soldering joint 86. The piezoelectric strip is actually within a hollow volume 89 of elongated insulation 87. The insulation 87 is glued to the cylinder 83 by an adhesive layer 88 in such a way as to ensure sealing of the volume 89. FIG. 9 shows the section designated by the dashed line "A" in FIG. 8. The voltage generated in the piezoelectric strip 80 can be measured between the stylet wire 85 and the central pacing lead conductor (not shown).

Figure 10:
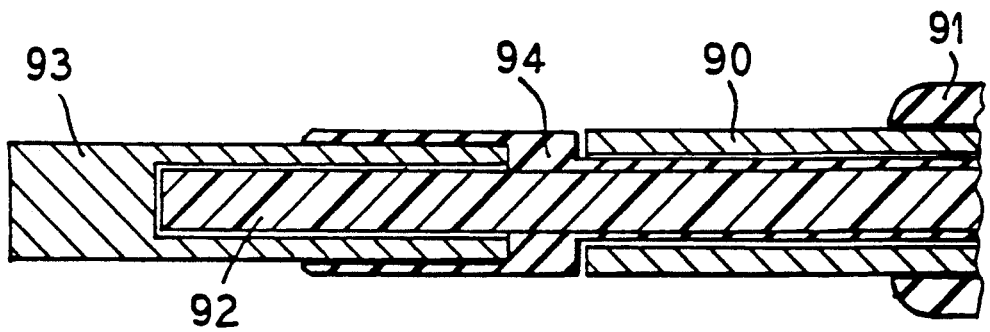
FIG. 10 is a cross-sectional view of the proximal end of a pacing lead having the tensiometric stylet inserted, constructed in accordance with the principles of the present invention.

In the embodiment of FIG. 10, there is shown a cross-section of the proximal end of a tensiometric stylet inserted within a pacing lead. The proximal terminal part of the lead has a connector pin 90, which is the terminal part of the central lead conductor (not shown) of a pacing lead. The connector pin 90 is insulated by a connector seal 91. A tensiometric stylet is inserted within the stylet channel and the stylet wire 92, (62 in FIG. 6, 73 in FIG. 7, 85 in FIG. 8), and is terminated with an additional connector pin 93. The pin 93 is isolated from the pin 90 by an insulation seal 94 which is actually the terminal part of the stylet wire insulation (63 in FIG. 6, 75 in FIG. 7, 87 in FIGS. 8 and 9).

In all of disclosed examples of the tensiometric stylet assembly, either the variable resistance or the piezoelectric voltage can be measured on the connector pins 90 and 93. Various lengths of stylets must be available in order to obtain the optimal position of distal end of the stylet within the lead in such a way as to position the tensiometric transducer in the lead bending area. It is possible to make a special preformed J-stylet for the atrial lead.

Strong cardiac contractions will cause the rhythmic lead distension having a large magnitude. Therefore, strong contractions accordingly will produce the large rhythmic changes of either the transducer resistance or the transducer voltage, depending on the type of transducer. In contrast, weak contractions such as occur in ventricular tachycardia and ventricular and atrial fibrillation will cause rhythmic lead distension having a small magnitude. Consequently, weak cardiac contractions will produce small rhythmic changes of either the transducer resistance or the transducer voltage, depending on the type of transducer.

Moreover, the transducer signal frequency corresponds with the frequency of cardiac contractions. Although some mechanical filtration will be caused by the elasticity of the lead, which attenuates the transfer of the mechanical energy from the myocardium to the transducer, the frequency spectra of the tensiometric transducers signal sufficiently represent the frequency spectra of myocardial contractions at the place of mechanical coupling between the lead and the heart. The pacing lead has the primary coupling point at the tip, but it may happen that there is some mechanical coupling proximally in the ventricle, especially when the fibrous channel is developed. The mechanical coupling of disclosed tensiometric defibrillator patch is ideal, because the tensiometric transducer is mechanically coupled to the heart directly and there is no attenuation of myocardial distension.

Not only because of different patterns of myocardial contractions in various cardiac arrhythmias, but also depending on the different possible modes of mechanical coupling between the myocardium and the tensiometric transducer, different patients will have different transducer signal waveform patterns and spectra. However, various diagnostic functions and rate responsive sensors can be used in the disclosed system. The atrial tensiometric lead can reliably detect the atrial contraction and therefore discriminate the atrial fibrillation from the sinus rhythm. The ventricular tensiometric lead or tensiometric patch can reliably detect the ventricular contractions and therefore diagnose ventricular tachycardia as well as fibrillation. Appropriate signal processing of the tensiometric transducers signal and measurements relatively to the endocardial electrogram detected by the same lead can be used to achieve a rate responsive sensor. For instance, circulatory catecholamines increase the contraction velocity during physical stress. A more sophisticated system may be achieved if more tensiometric transducers are implanted. If a tensiometric lead and a tensiometric patch are implanted as part of an implantable automatic cardioverter-defibrillator system, the timing sequence of ventricular contractions may be measured. The lead implanted in the right ventricular apex is primarily influenced by the right ventricular dynamics, while the patch sutured or glued to the left ventricular wall is primarily deformed by means of the left ventricular muscle forces. In various tachycardias the contraction timing sequence between the right and the left ventricle is different and also specific for a certain kind of tachycardia. If the timing between the sensed cardiac electrogram by means of the lead electrode and the contraction sequence is measured, the very important timing intervals may be obtained which have specific value in specific tachycardia. If the electrotherapy system also includes an atrial lead, the combination of timing intervals measurement is even more powerful in enabling the exact classification of ventricular as well as supraventricular arrhythmias.

Figure 11:
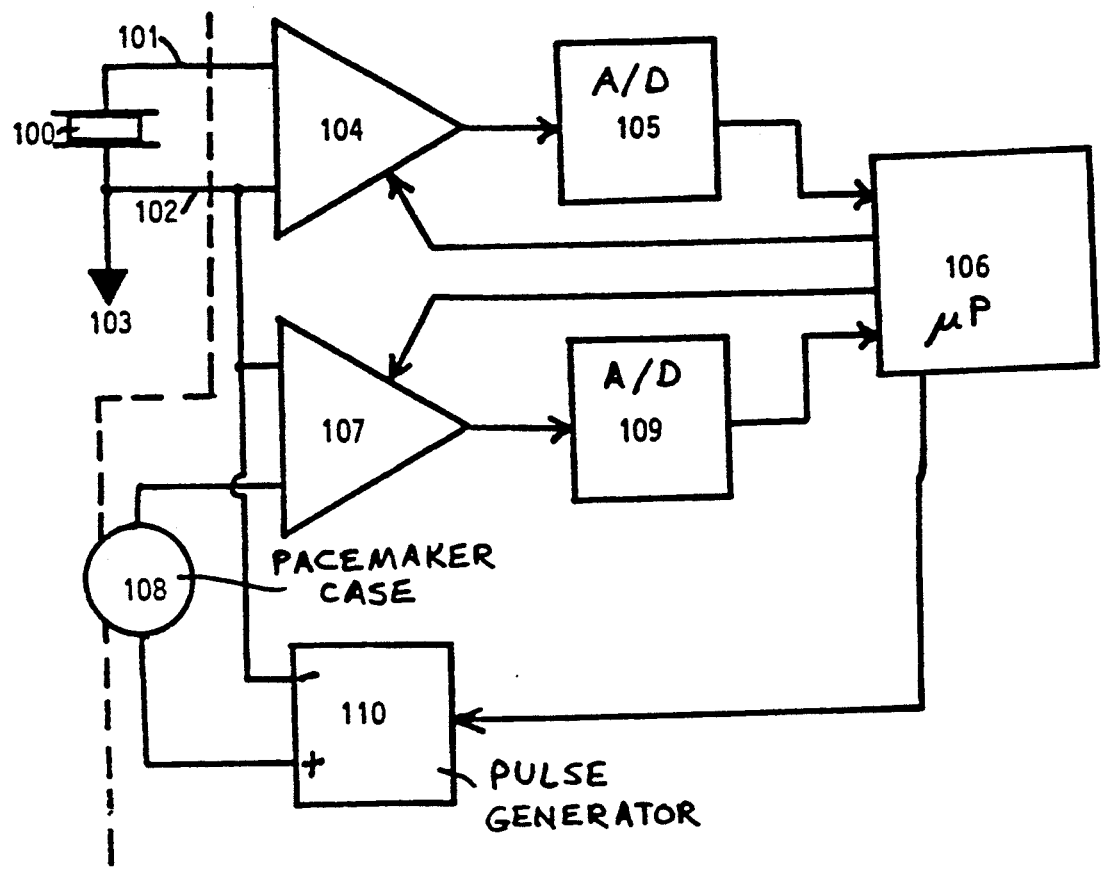
FIG. 11 is a simplified block diagram of an electrotherapy device having tensiometric lead constructed in accordance with the principles of the present invention.

FIG. 11 shows a simplified block diagram of an embodiment of a unipolar cardiac pacemaker having a tensiometric lead connected thereto. The lead has a piezoelectric tensiometric transducer 100 connected to the lead conductors 101 and 102, as well as the pacing-sensing electrode 103. The signal of the transducer 100 such as the Kynar ® Piezo Foil is supplied to a charge coupled amplifier 104. The output of the amplifier 104 is connected to the input of an analog-to-digital converter (or voltage-to-frequency converter) 105 in order to prepare the signal for processing within the microprocessor circuit 106 which controls the function of the entire pacemaker. The spontaneous rhythm signal, i.e., intracardiac electrogram, is supplied through the lead conductor 102 and the pacemaker case 108 to a band-pass filter-amplifier 107 which is controlled by the microprocessor 106. The signal out of the amplifier 107 is supplied to the input of the analog-to-digital converter 109 to generate digital information about the intracardiac signal for processing within the microprocessor 106. A microprocessor-controlled pulse generator 110 provides the electrotherapy signal, and is connected to the pacemaker case 108 with its positive pole and to the electrode 103 with its negative pole. A dashed line schematically separates the circuits inside of the pacemaker from the outside of the pacemaker. Although not shown in FIG. 11, it is known in the art that the lead conductors 101 and 102 are connected to the pacemaker by means of a connector assembly.

Figure 12:
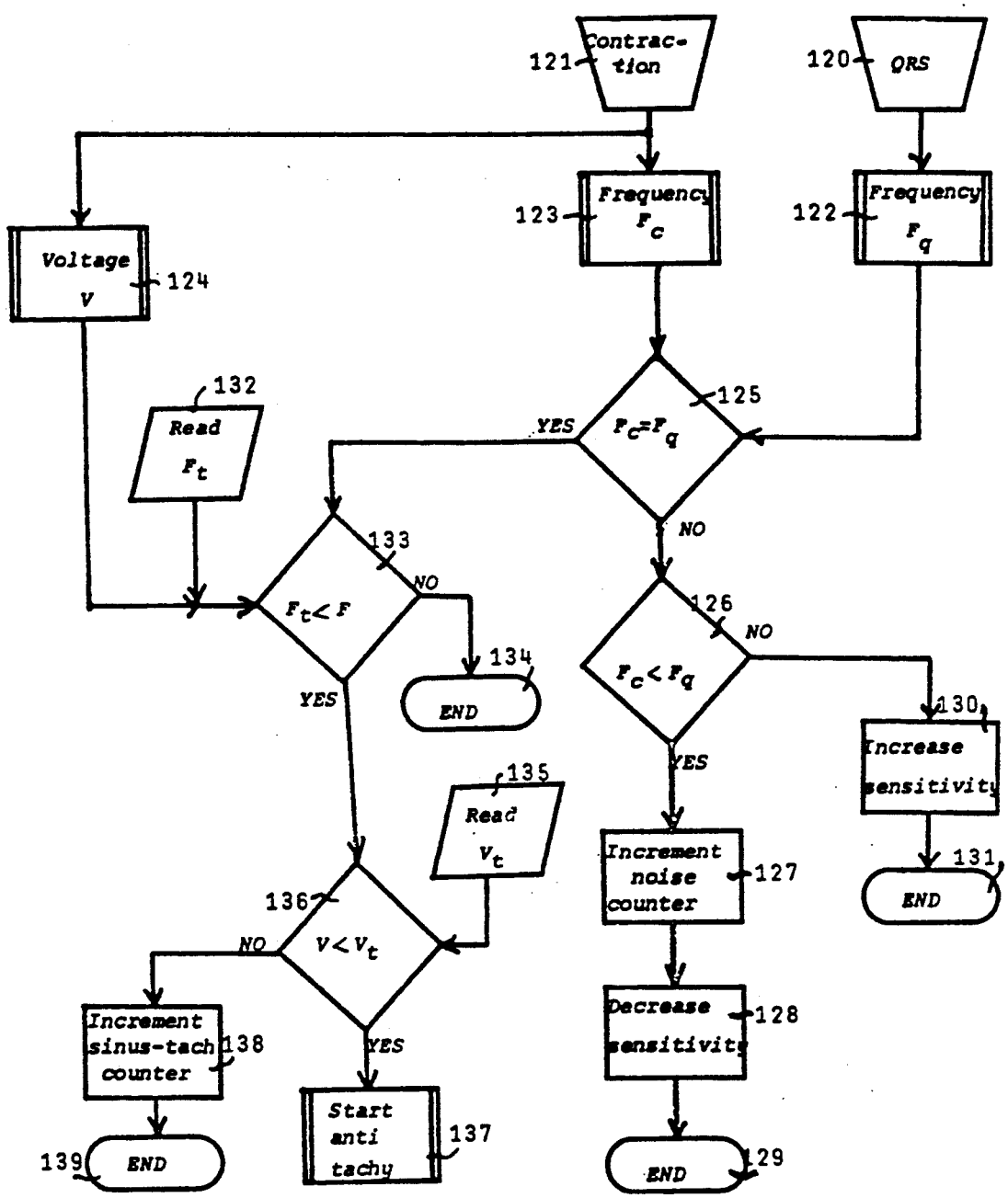
FIG. 12 is a flow chart illustrating how the microprocessor of the electrotherapy device of FIG. 11 polls various functions to detect pathologic tachycardia.

FIG. 12 shows a simple flow chart diagram illustrating how the microprocessor 106 polls various functions of the pacemaker in order to obtain the classification of tachycardias, i.e., differentiation between the sinus and pathologic tachycardia. It is assumed that pathologic tachycardia produces lower amplitude voltage in the tensiometric transducer in comparison with sinus tachycardia. The start of the software subroutine is initiated by the occurrence of the intracardiac QRS signal 120 which is followed by a cardiac contraction 121 sensed by means of the tensiometric transducer 100. The frequency $F_q$ of the electrical event and the frequency $F_c$ of the mechanical event are respectively calculated in subroutines 122 and 123. The voltage V of the tensiometric transducer is also calculated by a subroutine 124. Normally there is a subsequent delay of the mechanical event, i.e., cardiac contraction, which is a consequence of the electrical event, i.e., cardiac depolarization. However, the frequencies of the electrical and mechanical events must be equal in normal as well as in pathologic cardiac rhythm. Therefore, the frequencies $F_q$ and $F_c$ are compared at 125. If these are not equal, there is a malfunction of the pacing system. If the frequency of electrical events is higher (as determined at 126) than the frequency of mechanical events, it is likely that the pacemaker is sensing noise. Therefore, a noise events counter 127 is incremented and the sensitivity of the amplifier 107 is decreased at 128 in order to prevent oversensing. The software routine is ended (129), and may be initiated again. If the frequency of mechanical events is higher (as determined at 126) than the frequency of electrical events, it is likely that undersensing occurred and therefore the sensitivity is increased at 130, in order to establish the proper sensing which ends the routine (131), which may be initiated again. If the frequencies $F_q$ and $F_c$ are equal (125) the routine continues so as to differentiate the pathologic from sinus rhythm. The preprogrammed value of minimum tachycardia frequency $F_t$ is read at 132 from a memory for comparison at 133. If the frequency $F=F_q=F_c$ of cardiac rhythm does not exceed the minimum tachycardia frequency $F_t$, the routine may be ended (134) for next initiation. If the frequency F is higher than the frequency $F_t$, the cardiac rhythm is considered to be the tachycardia. Therefore, the preprogrammed value of maximum voltage $V_t$ of the tensiometric transducer in pathologic tachycardia is read at 135 from the memory for comparison at 136 with the measured value V from 124. If the measured voltage V is lower than the maximal pathologic tachycardia voltage $V_t$, an anti-tachycardia electrotherapy subroutine 137 will be initiated. If the measured tensiometric voltage V is higher than the maximal pathologic tachycardia voltage $V_t$, the tachycardia is considered to be provoked by normal patient exercise. Therefore, the sinus tachycardia event counter 138 is incremented and the routine is ended (139) for further possible initiation.

Although further modifications and changes may be suggested by those skilled in the art, it is the intention of the inventor to embody within the patent warranted hereon all changes and modifications as reasonably and properly come within the scope of his contribution to the art.

I claim as my invention:

1. A method for administering electrotherapy to cardiac tissue, said cardiac tissue exhibiting mechanical activity having a mechanical frequency and electrical activity having an electrical frequency, said method comprising the steps:

sensing in vivo the electrical frequency of said electrical activity;

tensiometrically sensing in vivo the mechanical frequency of said mechanical activity and generating a voltage amplitude corresponding to said mechanical activity;

comparing the sensed electrical and mechanical frequencies;

if the sensed electrical and mechanical frequencies are equal, comparing the equal frequencies to a minimum tachycardia frequency;

if said equal frequencies exceed said minimum tachycardia frequency, comparing said voltage amplitude with a maximum pathological tachycardia voltage; and if said voltage amplitude is less than said maximum pathological tachycardia voltage, administering anti-tachycardia electrotherapy to said cardiac tissue.

2. A method as claimed in claim 1 wherein the step of administering anti-tachycardia electrotherapy to said cardiac tissue is further defined by administering an anti-tachycardia pacing sequence to said cardiac tissue.

3. A method as claimed in claim 1 comprising the additional steps of:

sensing said electrical frequency with an adjustable sensitivity; and if the sensed electrical frequency is higher than the sensed mechanical frequency, decreasing said sensitivity.

4. A method as claimed in claim 1 comprising the additional steps of:

sensing said electrical frequency with an adjustable sensitivity; and if the sensed mechanical frequency is higher than the sensed electrical frequency, increasing said sensitivity.

5. An apparatus for administering electrotherapy to cardiac tissue, said cardiac tissue exhibiting mechanical activity having a mechanical frequency and electrical activity having an electrical frequency, said apparatus comprising:

means for sensing in vivo the electrical frequency of said electrical activity;

tensiometric means for sensing in vivo the mechanical frequency of said mechanical activity and for generating a voltage amplitude corresponding to said mechanical activity;

means for comparing the sensed electrical and mechanical frequencies;

means for comparing the sensed electrical and mechanical frequencies to a minimum tachycardia frequency if the sensed electrical and mechanical frequencies are equal;

means for comparing said voltage amplitude with a maximum pathological tachycardia voltage if the sensed electrical and mechanical frequencies are equal and exceed said maximum tachycardia frequency; and means for administering anti-tachycardia electrotherapy to said cardiac tissue if said sensed voltage amplitude is less than said maximum pathological tachycardia voltage.

6. An apparatus as claimed in claim 5 wherein said means for administering anti-tachycardia electrotherapy to said cardiac tissue is a means for administering an anti-tachycardia pacing sequence to said cardiac tissue.

7. An apparatus as claimed in claim 5 wherein said means for sensing in vivo the electrical frequency of said cardiac activity includes an amplifier having an adjustable sensitivity; and means for decreasing the sensitivity of said amplifier if the sensed electrical frequency is higher than the sensed mechanical frequency.

8. An apparatus as claimed in claim 5 wherein said means for sensing in vivo the electrical frequency of said cardiac activity includes an amplifier having an adjustable sensitivity, and means for increasing the sensitivity of said amplifier if the sensed mechanical frequency is higher than the sensed electrical frequency.

* * * * *